(12) United States Patent
Wang

(10) Patent No.: US 9,637,424 B1
(45) Date of Patent: May 2, 2017

(54) HIGH OCTANE GASOLINE AND PROCESS FOR MAKING SAME

(71) Applicant: ExxonMobil Research and Engineering Company, Annandale, NJ (US)

(72) Inventor: Kun Wang, Bridgewater, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 0 days.

(21) Appl. No.: 15/388,030

(22) Filed: Dec. 22, 2016

Related U.S. Application Data

(63) Continuation-in-part of application No. 14/956,477, filed on Dec. 2, 2015.

(60) Provisional application No. 62/092,485, filed on Dec. 16, 2014.

(51) Int. Cl.
| | |
|---|---|
| *C07C 2/76* | (2006.01) |
| *C07C 2/82* | (2006.01) |
| *C07C 29/00* | (2006.01) |
| *C10G 53/14* | (2006.01) |
| *C07C 2/86* | (2006.01) |
| *C10L 1/06* | (2006.01) |
| *C10L 10/10* | (2006.01) |
| *C07C 407/00* | (2006.01) |
| *C07C 29/48* | (2006.01) |

(52) U.S. Cl.
CPC .............. *C07C 2/862* (2013.01); *C07C 29/48* (2013.01); *C07C 407/00* (2013.01); *C10L 1/06* (2013.01); *C10L 10/10* (2013.01); *C10L 2200/0423* (2013.01); *C10L 2270/023* (2013.01)

(58) Field of Classification Search
CPC .. C07C 2/76; C07C 2/82; C07C 29/00; C10G 53/14
USPC .................. 585/700, 709; 208/49; 568/909.8
See application file for complete search history.

(56) References Cited

U.S. PATENT DOCUMENTS

| | | |
|---|---|---|
| 2,645,461 A | 7/1958 | Winkler et al. |
| 3,478,108 A | 11/1969 | Grane |
| 3,594,320 A | 7/1971 | Orkin |
| 3,775,325 A | 11/1973 | Kerfoot et al. |
| 3,862,024 A | 1/1975 | Favis |
| 4,140,619 A | 2/1979 | van der Wiel et al. |
| 4,175,278 A | 11/1979 | Sato et al. |
| 4,408,081 A | 10/1983 | Foster |
| 4,594,172 A | 6/1986 | Sie |
| 4,618,737 A | 10/1986 | Chester et al. |
| 4,883,581 A | 11/1989 | Dickakian |
| 4,911,821 A | 3/1990 | Katzer et al. |
| 4,913,794 A | 4/1990 | Le et al. |
| 4,919,788 A | 4/1990 | Chen et al. |
| 4,975,177 A | 12/1990 | Garwood et al. |
| 4,990,713 A * | 2/1991 | Le .................. C10G 50/02 585/332 |
| 4,997,543 A | 3/1991 | Harandi et al. |
| 5,008,460 A | 4/1991 | Garwood et al. |
| 5,021,142 A | 6/1991 | Bortz et al. |
| 5,037,528 A | 8/1991 | Garwood et al. |
| 5,149,885 A | 9/1992 | Jubin, Jr. |
| 5,162,593 A | 11/1992 | Maffia et al. |
| 5,171,916 A | 12/1992 | Le et al. |
| 5,243,084 A | 9/1993 | Cochran et al. |
| 5,271,825 A | 12/1993 | Bortz et al. |
| 5,288,919 A | 2/1994 | Faraj |
| 5,306,416 A | 4/1994 | Le et al. |
| 5,345,009 A | 9/1994 | Sanderson et al. |
| 5,705,724 A | 1/1998 | Collins et al. |
| 5,750,480 A | 5/1998 | Xiong et al. |
| 7,034,189 B1 | 4/2006 | Kollar |
| 7,723,556 B2 | 5/2010 | Elomari et al. |
| 7,732,654 B2 | 6/2010 | Elomari et al. |
| 7,973,204 B2 | 7/2011 | Elomari et al. |
| 2008/0253936 A1 | 10/2008 | Abhari |
| 2016/0168048 A1 | 6/2016 | Wang et al. |

FOREIGN PATENT DOCUMENTS

| | | |
|---|---|---|
| CA | 1103913 A | 6/1981 |
| CA | 2098995 A1 | 7/1992 |
| DE | 2453863 A1 | 5/1975 |
| DE | 298521 A5 | 2/1992 |
| EP | 0104729 A2 | 4/1984 |
| FR | 2210656 A1 | 7/1974 |
| FR | 2210657 A1 | 7/1974 |
| JP | 49034903 A | 3/1974 |
| JP | 60108495 A | 6/1985 |

(Continued)

OTHER PUBLICATIONS

PcT/US2015/063394 International Search Report and Written Opinion dated Mar. 18, 2016.

Wallner at al., "Analytical Assessment of C2-C8 Alcohols as Spark-Ignition Engine Fuels", Proceedings of the FISITA 2012 World Automotive Congress. Nov. 7, 2012, pp. 15-26, vol. 3, Springer Unknown, "Advanced Motor Fuels", Implementing Agreement for Advanced Motor Fuels, http://www.iea-amf.org/content/fuel_information/butanol/properties.

Ghosh et at., "Development of a Detailed Gasoline Composition-Based Octane Model", Industrial & Engineering Chemistry Research, Nov. 24, 2005, pp. 337-345, vol. 45, iss, 1, ACS Publications.

(Continued)

*Primary Examiner* — Thuan D Dang
(74) *Attorney, Agent, or Firm* — Andrew T. Ward

(57) ABSTRACT

A process for converting light paraffins to a high octane gasoline composition is disclosed. The process involves: (1) oxidation of iso-paraffins to alkyl hydroperoxides and alcohol; (2) conversion of the alkyl hydroperoxides and alcohol to dialkyl peroxides; and (3) radical coupling of iso-paraffins using the dialkyl peroxides as radical initiators, thereby forming gasoline-range molecules. Fractionation of the gasoline-range molecules can then be used to isolate high octane gasoline fractions having a road octane number [(RON+MON)/2] greater than 110.

12 Claims, No Drawings

(56) References Cited

FOREIGN PATENT DOCUMENTS

| NL | 7510598 | A  | 3/1977  |
|----|---------|----|---------|
| PL | 63556   | Y1 | 12/1969 |
| SU | 51012802| A  | 1/1976  |
| SU | 1068467 | A1 | 1/1984  |
| SU | 438293  | A1 | 11/1984 |
| SU | 1525196 | A1 | 11/1989 |
| SU | 1778148 | A1 | 11/1992 |
| SU | 1799902 | A1 | 3/1993  |
| SU | 1810378 | A1 | 4/1993  |

OTHER PUBLICATIONS

Perdih et al., "Topological Indices Derived from Parts of a Universal Matrix", Acta Chimica Slovenica, Apr. 25, 2006, pp. 180-190, vol. 53, Slovenian Chemical Society.

Sust, "Studies on the synthesis of lubricating oils using olefins from technical C5-fractions", Energy Res., 1983, vol .8, iss.1, abstract only.

Grudzien, "Selective solvent separation of shale oil fractions to obtain raw material for polymerization", Koks, Smola, Gaz, 1971, pp. 336-339, vol. 16, iss. 12, abstract only.

Ouyang et al., "Production technique of synthetic hydrocarbon lube oil with coking top cycle oil", Runhuayou, 2001, pp. 17-20, vol. 15, iss. 5, abstract only.

Kuliev et al., "Production of lubricating oils by alkylation of an aromatic raw material", Sbornik Trudov—Akademiya Nauk Azerbaidzhanskol SSR, Institut Neftekhimicheskikh Protsessov im. Yu, G. Mamedalieva, 1973, pp. 128-128, vol. 5, abstract only.

Kuliev et al., "Manufacture of synthetic lubricating oils by alkylation of a secondary oil refining product", Chemische Technik, 1971, vol. 23, iss. 1, abstract only.

Takahashi et al., "Designed Oil Products from Cracked Bottom Oil", Bull Jap Petrol Inst, May 1971, pp. 103-108, vol. 13, iss. 1, abstract only.

Mursalova el al., "Alkylation of Benzene with a Wide Fraction of Alpha-Olefins (30 Degrees-250 Degrees C) Obtained by Cracking N-Paraffins (Separated in the Urea Dewaxing) of a Transformer Oil", Dokl Akad Nauk Azerb SSR, 1969; pp. 20-23, vol. 25, iss. 7, abstract only.

Kuliev, "Alkyl derivatives of petroleum hydrocarbons as lubricating oil basestocks", Khimiya I Tekhnologiya Topliv I Masel, 1997, pp. 34-35, vol. 6, abstract only.

Graves, "STRATCO Effluent Refrigerated H2SO4 Alkylation Process", Chapter 1.2 in Handbook of Petroleum Refining Processes, 3rd Ed., 2004. McGraw-Hill.

Roeseler, "UOP Alkylene Process for Motor Fuel", Chapter 1.3 in Handbook of Petroleum Refining Processes, 3rd Ed., 2004, McGraw-Hill.

Detrick et al., "UOP HF Alkylation Technology", Chapter 1.2 in Handbook of Petroleum Refining Processes, 3rd Ed., 2004, McGraw-Hill.

\* cited by examiner

HIGH OCTANE GASOLINE AND PROCESS FOR MAKING SAME

CROSS-REFERENCE TO RELATED APPLICATIONS

This application is a continuation-in-part of U.S. Ser. No. 14/956,477, filed Dec. 2, 2015, now allowed, which claims the benefit of provisional U.S. Ser. Nos. 62/092,485, filed on Dec. 16, 2014, each of which is incorporated by reference herein in its entirety.

BACKGROUND

The present invention relates to a process to upgrade light paraffins, preferably C2-C5, to high-octane gasoline. The process is particularly applicable to the upgrading of iso-paraffins, which are abundantly found in Natural Gas Liquids (NGL) and tight oils (produced from shale or sandstone), as well as fractions from various refining and/or chemical streams.

With the increasing production of shale gas and tight oils, the supply of light paraffins (e.g., C.2-C8, especially C2-C5 paraffins) is increasing at an unprecedented rate in the North America region; a large fraction (up to 30%) of NGL, for example, is C4/C5 paraffins. At the same time, demand for C4/C5 molecules is decreasing due to a number of factors: (1) steam crackers switching feed from light naphtha to ethane; (2) shrinkage of the gasoline pool in the North American market; and (3) a potential mandate for gasoline Reid Vapor Pressure (RVP) reduction. Although diluent use of C5s for heavy crude is predicted to grow somewhat, the supply of C4s/C5s is quickly outpacing demand and the imbalance will become worse with time.

Profitable dispositions for ethane (e.g., cracking to make ethylene) and propane (e.g., dehydrogenation to make propylene) exist. Upgrading C4/C5 paraffins to higher value and large volume products, while desirable, remains challenging. Conversion of C4/C5 paraffins to heavier hydrocarbon products such as gasoline, kerojet, diesel fuels, and lubricant basestocks would provide a large volume and higher value outlet to help alleviate the excess of light ends in the North American market. But there is no current commercial process directly converting light paraffins to heavier hydrocarbons such as these. Conventional upgrading practices first convert light paraffins to olefins via cracking or dehydrogenation, followed by olefin chemistries such as oligomerization or polymerization, alkylation, etc., to build higher molecular weight molecules. A number of technologies are known to convert light paraffins to aromatics such as BTX (benzene, toluene, and xylenes), including the Cyclar™ process developed by UOP and the M2-Forming process developed by Mobil Oil Corporation.

Currently, modern automobile gasoline engines require high octane fuel, and the demand for high octane gasoline is expected to continue to grow. Current high octane molecules from refining processes include aromatics, oxygenates, and alkylates. Current gasoline molecules from refining processes, with the exception of toluene, have a road octane number less than 110, such as the following typical road octane values: iso-butane 99.8; 2,3-dimethylbutane 100; 2,2,3-trimethylbutane 107.1; C8 trimethyls 101.9; benzene 100.8; toluene 110.7; C8+ aromatics 108.5-96; MTBE 106.2; TAME 106.5; and ethanol 100.4. Although aromatic molecules typically offer high octane, particulate emissions are a concern. Oxygenated high octane gasoline molecules such as ethanol have lower energy content (e.g., ethanol has ~82% of the volumetric energy content of gasoline) and can cause compatibility problems at high blending ratios. There is no commercial process to produce non-aromatic, non-oxygenated molecules with higher than 110 road octane. As such, there still remains a need for a process for producing higher octane, non-aromatic, non-oxygenated gasoline molecules, especially a process using readily available feedstocks, such as light paraffins.

SUMMARY

We have now found a novel process for producing high octane gasoline from abundant light paraffins. In a first embodiment of the present invention, the process involves: (1) oxidation of iso-paraffins to alkyl hydroperoxides and alcohol; (2) conversion of the alkyl hydroperoxides and alcohol to dialkyl peroxides; and (3) radical-initiated coupling of iso-paraffins using the dialkyl peroxides as radical initiators, thereby forming products comprising gasoline range molecules. Fractionation of the product can then isolate the gasoline fraction, which is substantially a C8 fraction having a road octane [(RON+MON)/2] greater than 110.

In another embodiment of the present invention, the process involves (1) oxidizing iso-butane to t-butyl hydroperoxide and t-butyl alcohol; (2) converting the t-butyl hydroperoxide and t-butyl alcohol to di-t-butyl peroxide; and (3) radical-initiated coupling iso-butane using the di-t-butyl peroxide as a radical initiator to form products comprising gasoline range molecules. This product is then fractionated to isolate the gasoline fraction, which is substantially a C8 fraction having a road octane [(RON+MON)/2] greater than 110.

In yet another embodiment of the present invention, a gasoline composition is disclosed consisting primarily of C8 paraffins, primarily 2,2,3,3-tetramethylbutane, and having a road octane number greater than 100 without the inclusion of aromatics or oxygenates.

DETAILED DESCRIPTION

The present invention relates to a process for making high octane gasoline from light paraffins. The process of the present invention involves three primary steps: (1) oxidizing one or more iso-paraffins to alkyl hydroperoxides and alcohol using air or oxygen; (2) converting the alkyl hydroperoxides and alcohol to dialkyl peroxide; and (3) radical-initiated coupling the iso-paraffin using the dialkyl peroxide as a radical initiator to form products comprising gasoline range molecules. This products are then fractionated to isolate the gasoline fraction having a road octane number [(RON+MON)/2] greater than 110.

In a preferred embodiment of the present invention, the iso-paraffin feedstock is iso-butane. The process proceeds as described generally above: (1) oxidizing the iso-butane to t-butyl hydroperoxide and t-butyl alcohol using air or oxygen; (2) converting the t-butyl hydroperoxide and t-butyl alcohol to di-t-butyl peroxide; and (3) radical-initated coupling of iso-butane using the di-t-butyl peroxide as a radical initiator to form products comprising gasoline range molecules. This products are then fractionated to isolate the gasoline fraction, which is a substantially C8 fraction having a road octane [(RON+MON)/2] greater than 110.

The chemistry of Steps 1-3 with respect to iso-butane feed is shown below in corresponding Equations 1-3, with accompanying Road octane values for the hydrocarbon products:

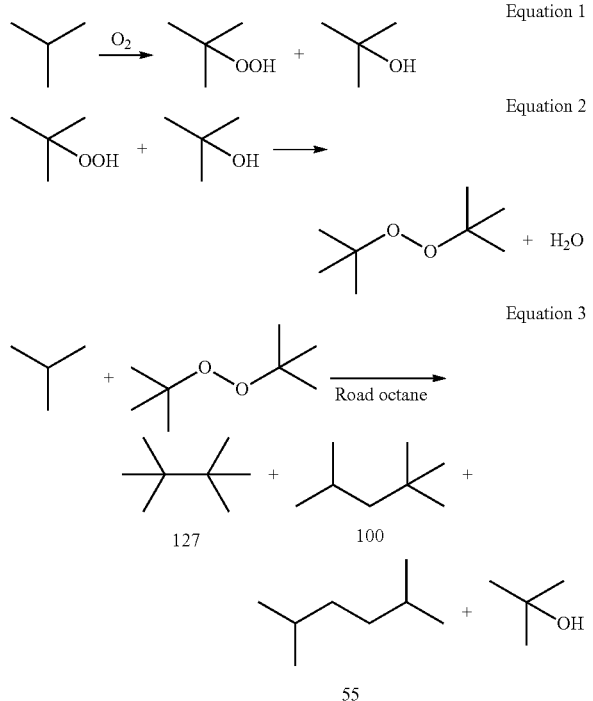

The net reaction of Equations 1-3 is oxygen (air) and iso-butane yielding heavier (C8) hydrocarbons comprising high octane gasoline, as well as water and t-butyl alcohol. As shown below in Table 1, Step 3 is highly selective to 2,2,3,3-tetramethylbutane (road octane number of ~127), thus creating an overall C8 fraction having exceptionally high octane. By controlling the reaction severity for radical coupling (Equation 3), higher molecular weight materials can also be obtained. Depending on the nature of the iso-paraffin used, the resulting alcohol can be used as high octane blend stock for gasoline, e.g., t-butyl alcohol (road octane of about 96) from iso-butane, or 2-methyl-2-butanol (road octane of about 90) from iso-pentane. Alternatively, the alcohols can be converted via dehydration to olefins as chemical products (e.g., iso-butylene), oligomerized or alkylated to gasoline and/or diesel range fuels, or etherified with an alcohol such as methanol or ethanol making ether as a gasoline blend (e.g., MTBE or ETBE from iso-butane).

Steps 1 and 2 have been previously described with respect to mixed paraffinic feedstocks in applicant's co-pending application, U.S. Publ. App. No. 2016/0168048, incorporated by reference herein in its entirety. U.S. Publ. App. No. 2016/0168048 describes a process to convert light paraffins to heavier hydrocarbons generally, for example, distillates and lubricant base stocks, using coupling chemistry analogous to Steps 1-3 described above. Whereas U.S. Publ. App. No. 2016/0168048 is directed to mixed paraffinic feed to create distillates and lubricant base stocks, the present invention utilizes analogous coupling chemistry to create a tailored paraffinic hydrocarbon fluid utilizing iso-paraffinic feedstock. U.S. Publ. App. No. 2016/0168048 further discloses upgrading raw refinery feeds, such as natural gas liquids, liquid petroleum gas, and refinery light gas such as light virgin naphtha (LVN) or light catalytic naphtha (LCN), using coupling chemistry.

Iso-butane oxidation in Step 1 is well-established commercially for making t-butyl hydroperoxide (TBHP) for propylene oxide manufacture, with variants of the process also described, for example, in U.S. Pat. No. 2,845,461; U.S. Pat. No. 3,478,108; U.S. Pat. No. 4,408,081 and U.S. Pat. No. 5,149,885. EP 0567336 and U.S. Pat. No. 5,162,593 disclose co-production of TBHP and t-butyl alcohol (TBA). As TBA is another reactant used in Step 2 of the present invention, the present inventive process scheme utilizes Step 1 as a practical source of these two reactants. Air (~21% oxygen), a mixture of nitrogen and oxygen containing 2-20 vol % oxygen, or pure oxygen, can be used for the oxidation, as long as the oxygen-to-hydrocarbon vapor ratio is kept outside the explosive regime. Preferably air is used as the source of oxygen. Typical oxidation conditions for Step 1 of the present invention are: 110-150° C. (preferably 130 to 140° C., at a pressure of about 300-800 psig (preferably about 450-550 psig), with a residence time of 2-24 hours (preferably 6-8 h), to give a targeted conversion of 15%-70% (preferably 30-50%). Selectivity to TBHP of 50-80% and to TBA of 20-50% is typical.

In Step 2, the conversion of the TBHP and TBA to di-t-butyl peroxide (DTBP) is performed using an acid catalyst. For example, U.S. Pat. No. 5,288,919 describes the use of an inorganic heteropoly and/or isopoly acid catalyst (such as for the reaction of TBA with TBHP. The conjoint production of DTBP and TBA from TBHP is also described in U.S. Pat. No. 5,345,009. A preferred configuration for the present invention uses reactive distillation where product water is continuously removed as overhead by-product. Typical reaction temperature is in the range of 50-200° C., preferably 60-150° C., more preferably 80-120° C. The TBHP to TBA mole ratio is in the range of 0.5-2, preferably 0.8-1.5, more preferably 0.9-1.1. The reaction can be performed with or without a solvent. Suitable solvents comprise hydrocarbons having a carbon number greater than 3, such as paraffins, naphthenes, or aromatics. Conveniently, the unreated iso-butane from Step 1 can be used as solvent for Step 2. Pressure for the reaction is held at appropriate ranges to ensure the reaction occurs substantially in the liquid phase, for example, 0-300 psig, preferably 5-100 psig, more preferably 15-50 psig. An acid catalyst such as Amberlyst™ resin, Nafion™ resin, aluminosilicates, acidic clay, zeolites (natural or synthetic), silicoaluminophosphates (SAPO), heteropolyacids, acidic oxides such as tungsten oxide on zirconia, molybdenum oxide on zirconia, sulfuated zirconia, liquid acids such sulfuric acid, or acidic ionic liquids may be used in Step 2/Equation 2 to promote the conversion of TBHP and TBA into DTBP.

In Step 3/Equation 3, DTBP is introduced to a coupling reactor to initiate free radical coupling of iso-butane feed. Typical reaction conditions for Step 3 of the present invention are: 100-170° C. (preferably about 145-155° C.), with pressure maintained to ensure that iso-butane stays in the liquid or supercritical phase, typically 700-1500 psig (preferably about 850-950 psig). Residence time is normally in the range of 2-24 hours (preferably 4-16 hours). The molar ratio of DTBP to iso-butane to be coupled is in the range of about 0.01-100, preferably in the range of about 0.05-10, and more preferably in the range of 0.1-2. Complete conversion of DTBP is normally achieved in this step.

Following Step 3, the mixed products are then fractionated to remove unreacted iso-butane and TBA, byproduct acetone, and to separate high octane gasoline as well as jet-range hydrocarbons.

EXAMPLE

In order to provide a better understanding of the foregoing disclosure, the following non-limiting example is offered.

Although the example may be directed to specific embodiments, they are not to be viewed as limiting the invention in any specific respect.

This example illustrates the general procedure for coupling iso-butane using DTBP to form high octane gasoline. In a 300 cc autoclave the following were loaded: 100 cc (59.5 g) of iso-butane (Airgas, instrument grade) and 56 g of DTBP (trade name Luperox DI from Aldrich Chemicals, 98%). The autoclave was sealed, connected to a gas manifold, and pressurized with 600 psig nitrogen. The reactor content heated under stirring (500 rpm) at a rate of 2° C./min to 150° C. and held for 4 hours. The heat was turned off and the autoclave allowed to cool down to room temperature. A sample was taken and analyzed by GC, showing complete conversion of DTBP. The autoclave was opened and the reactor content collected at the end of the run, recovering 88% of the materials loaded. The products were analyzed by GC. The run was repeated using different loadings of DTBP. The results are shown below in Table 1.

TABLE 1

| Reaction temperature (° C.) | 150 | 150 | 150 | 150 | 135 | 135 | 135 | 135 |
|---|---|---|---|---|---|---|---|---|
| Time (h) | 4 | 4 | 4 | 4 | 21 | 21 | 21 | 21 |
| iso-butane loading, g | 59.4 | 59.4 | 59.4 | 59.4 | 59.4 | 59.4 | 59.4 | 59.4 |
| DTBP loading, g | 56.0 | 40.0 | 24.0 | 16.0 | 56.0 | 40.0 | 24.0 | 16.0 |
| HC wt. sel. (%) | | | | | | | | |
| 2,2,4-trimethylpentane | 13.48 | 14.26 | 13.05 | 15.48 | 14.61 | 16.50 | 16.38 | 16.08 |
| 2,4,4-trimethyl-1-pentene | 0.22 | 0.46 | 1.64 | 3.42 | 0.17 | 0.20 | 0.82 | 1.52 |
| 2,2,3,3-tetramethylbutane | 19.35 | 18.88 | 18.67 | 18.67 | 17.55 | 19.63 | 17.44 | 16.77 |
| 2,4,4-trimethyl-2-pentene | 0.29 | 0.35 | 0.48 | 0.55 | 0.16 | | | |
| 2,2,3-trimethlypentane | 1.32 | | | | 0.28 | 0.32 | 0.42 | 0.47 |
| 2,5-dimethylhexane | 1.18 | 1.49 | 1.55 | 1.48 | 1.42 | 1.29 | 1.29 | 1.14 |
| 4,4-dimethyl-2-pentanone | 0.94 | 11.06 | 9.14 | 9.08 | 0.46 | 4.84 | 7.48 | 6.29 |
| 2,2,4,4-tetramethylpentane | 0.76 | 0.56 | 0.30 | 0.21 | 0.40 | 0.46 | 0.22 | 0.15 |
| 2,2,4-trimethylhexane | 1.44 | 0.65 | 0.51 | 0.42 | 1.00 | 0.43 | 0.25 | 0.20 |
| 2,4,4-trimethylhexane | 0.40 | 1.41 | 1.32 | 1.16 | 0.27 | 1.12 | 0.84 | 0.72 |
| 2,2,3,3-tetramethylpentane | 1.55 | 0.58 | 0.93 | 1.12 | 0.74 | 0.17 | 0.44 | 0.56 |
| C9 | 12.83 | 10.69 | 8.39 | 6.81 | 8.52 | 7.99 | 8.82 | 4.57 |
| C12 | 5.51 | 8.33 | 14.21 | 16.40 | 6.98 | 7.83 | 15.25 | 20.57 |
| C16+ | 33.29 | 36.49 | 35.20 | 30.94 | 42.09 | 37.81 | 34.43 | 34.57 |
| Oxygenates wt. sel. (%) | | | | | | | | |
| Acetone | 30.6 | 28.7 | 22.6 | 22.0 | 21.0 | 21.7 | 15.8 | 13.2 |
| t-Butanol | 69.4 | 71.3 | 77.4 | 78.0 | 79.0 | 78.3 | 84.2 | 86.8 |
| gasoline fraction (RON + MON)/2 | 113.1 | 112.5 | 112.3 | 111.0 | 112.0 | 112.4 | 111.4 | 111.2 |

As demonstrated in Table 1, a gasoline composition comprising 2,2,3,3-tetramethylbutane and having road octane [(RON+MON)/2] greater than 110 can be produced from certain teachings of the present invention. This road octane number is achieved without the addition of aromatics or oxygenates. One of skill in the art will appreciate that key variables, including reaction temperature, molar ratio of DTBP to iso-butane, and residence time, can be adjusted to optimize and tailor the gasoline fraction for specific applications.

ADDITIONAL EMBODIMENTS

Embodiment 1

A process for the conversion of iso-paraffins to gasoline-range molecules, comprising oxidizing a first feed stream comprising one or more iso-paraffins to form alkyl hydroperoxides and alcohol, catalytically converting the alkyl hydroperoxides and alcohols to dialkyl peroxides, and coupling a second feed stream comprising one or more iso-paraffins using the dialkyl peroxides as a radical initiator to create gasoline-range molecules.

Embodiment 2

A process according to embodiment 1, further comprising fractionating the gasoline-range molecules to isolate a desired gasoline fraction.

Embodiment 3

A process according to any of the previous embodiments, wherein the one or more iso-paraffins in the first feed stream and in the second feed stream is independently selected from iso-butane, iso-pentane, and mixtures thereof.

Embodiment 4

A process according to any of the previous embodiments, wherein the one or more iso-paraffins in the first feed stream is iso-butane.

Embodiment 5

A process according to any of the previous embodiments, wherein the one or more iso-paraffins in the second feed stream is iso-butane.

Embodiment 6

A process for the conversion of iso-butane to paraffinic gasoline-range molecules, comprising, oxidizing iso-butane to form t-butyl hydroperoxide and t-butyl alcohol, catalytically converting the t-butyl hydroperoxide and the t-butyl alcohol to di-t-butyl peroxide, and coupling iso-butane using the di-t-butyl peroxide as a radical initiator to form gasoline-range molecules.

Embodiment 7

A process according to embodiment 6, further comprising fractionating the gasoline-range molecules to isolate a desired gasoline fraction.

Embodiment 8

A process according to any of the previous embodiments, wherein the desired gasoline fraction comprises substantially all C8 paraffins.

Embodiment 9

A process according to any of the previous embodiments, wherein the desired gasoline fraction comprises substantially all C8 and C9 paraffins.

Embodiment 10

A process according to any of the previous embodiments, wherein the desired gasoline fraction has a road octane number [(RON+MON)/2)] greater than about 110.

Embodiment 11

A process according to any of the previous embodiments, wherein the desired gasoline fraction has a road octane number greater than about 111.

Embodiment 12

A process according to any of the previous embodiments, wherein the desired gasoline fraction has a road octane number greater than about 112.

Embodiment 13

A process according to any of the previous embodiments, wherein the desired gasoline fraction comprises substantially all C8 paraffins.

Embodiment 14

A process according to any of the previous embodiments, wherein the desired gasoline fraction comprises substantially all C8 and C9 paraffins.

Embodiment 15

A process according to any of the previous embodiments, wherein the desired gasoline fraction comprises 2,2,3,3-tetramethylbutane.

Embodiment 16

A process according to any of the previous embodiments, wherein the desired gasoline fraction comprises 2-95 vol % 2,2,3,3-tetramethylbutane.

Embodiment 17

A process according to any of the previous embodiments, wherein the desired gasoline fractrion comprises 5-90 vol % 2,2,3,3-tetramethylbutane.

Embodiment 18

A process according to any of the previous embodiments, wherein the desired gasoline fractrion comprises 50-80 vol % 2,2,3,3-tetramethylbutane.

Embodiment 19

A high octane gasoline composition, comprising a desired gasoline fraction prepared according to any of the previous embodiments.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings therein. It is therefore evident that the particular embodiments disclosed above may be altered or modified and all such variations are considered within the scope and sprit of the present invention. Unless otherwise indicated, all numbers expressing quantities of ingredients, properties, reaction conditions, and so forth, used in the specification and claims are to be understood as approximations based on the desired properties sought to be obtained by the present invention. Whenever a numerical range with a lower limit and an upper limit is disclosed, a number falling within the range is specifically disclosed. Moreover, the indefinite articles "a" or "an", as used in the claims, are defined herein to mean one or more than one of the element that it introduces.

The invention claimed is:

1. A process for the conversion of iso-paraffins to gasoline-range molecules, comprising:
    (a) oxidizing a first feed stream comprising one or more iso-paraffins to form alkyl hydroperoxides and alcohol;
    (b) catalytically converting the alkyl hydroperoxides and alcohols to dialkyl peroxides;
    (c) providing a second feed stream comprising iso-paraffins to couple iso-paraffins with other iso-paraffins using the dialkyl peroxides as a radical initiator to create gasoline-range molecules including 2,2,3,3-tetramethylbutane;
    (d) fractionating the gasoline-range molecules to isolate a desired gasoline fraction having a road octane number [RON+MON)/2)] greater than about 110.

2. The process of claim 1, wherein the desired gasoline fraction comprises substantially all C8 paraffins.

3. The process of claim 1, wherein the desired gasoline fraction comprises substantially all C8 and C9 paraffins.

4. The process of claim 1, wherein the desired gasoline fraction has a road octane number greater than about 111.

5. The process of claim 1, wherein the desired gasoline fraction has a road octane number greater than about 112.

6. The process of claim 1, wherein the one or more iso-paraffins in the first feed stream and in the second feed stream is independently selected from iso-butane, iso-pentane, and mixtures thereof.

7. The process of claim 1, wherein the one or more iso-paraffins in the first feed stream is iso-butane.

8. The process of claim 1, wherein the one or more iso-paraffins in the second feed stream is iso-butane.

9. A process for the conversion of iso-butane to paraffinic gasoline-range molecules, comprising:
    (a) oxidizing iso-butane to form t-butyl hydroperoxide and t-butyl alcohol;
    (b) catalytically converting the t-butyl hydroperoxide and the t-butyl alcohol to di-t-butyl peroxide;
    (c) coupling iso-butane with another isobutane using the di-t-butyl peroxide as a radical initiator to form gasoline-range molecules including 2,2,3,3-tetramethylbutane;
    (d) fractionating the gasoline-range molecules to isolate a desired gasoline fraction having a road octane number [RON+MON)/2)] greater than about 110.

10. The process of claim 9, wherein the desired gasoline fraction comprises substantially all C8 paraffins.

11. The process of claim 9, wherein the desired gasoline fraction has a road octane number greater than about 111.

12. The process of claim 9, wherein the desired gasoline fraction has a road octane number greater than about 112.

* * * * *